US006803470B2

United States Patent
Lowe, III et al.

(10) Patent No.: US 6,803,470 B2
(45) Date of Patent: Oct. 12, 2004

(54) 2-AMINO-6-(2,4,5-SUBSTITUTED-PHENYL)-PYRIDINES

(75) Inventors: John A. Lowe, III, Stonington, CT (US); Robert A. Volkmann, Mystic, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/266,249

(22) Filed: Oct. 8, 2002

(65) Prior Publication Data

US 2003/0087891 A1 May 8, 2003

Related U.S. Application Data

(60) Provisional application No. 60/328,252, filed on Oct. 10, 2001, and provisional application No. 60/328,253, filed on Oct. 10, 2001.

(51) Int. Cl.⁷ ..................... C07D 401/12; C07D 213/38

(52) U.S. Cl. ..................... 546/268.1; 546/311

(58) Field of Search ............... 546/268.1, 311

(56) References Cited

U.S. PATENT DOCUMENTS

| 6,235,747 B1 | 5/2001 | Lowe, III et al. |
| 6,465,491 B2 | 10/2002 | Lowe, III et al. |

FOREIGN PATENT DOCUMENTS

| WO | WO9736871 | 10/1997 |
| WO | WO9834919 | 8/1998 |
| WO | 00/71107 | * 11/2000 |

* cited by examiner

*Primary Examiner*—Patricia L. Morris
(74) *Attorney, Agent, or Firm*—P. C. Richardson; L. B. Ling; K. L. Konstas

(57) ABSTRACT

The present invention relates to the compounds 6-[4-(N-methyl-3-azetidinoxy)-5-ethyl-2-methoxy-phenyl]-pyridin-2-ylamine, 6-[4-(N,N-dimethylaminomethyl)-5-ethyl-2-methoxy-phenyl]-pyridin-2-ylamine, 6-[4-(N-methylaminomethyl)-5-ethyl-2-methoxy-phenyl]-pyridin-2-ylamine and 6-[4-(3-azetidinoxy)-5-ethyl-2-methoxy-phenyl]-pyridin-2-ylamine, and the pharmaceutically acceptable salts thereof, to pharmaceutical compositions containing such compounds and to the use of such compounds in the treatment and prevention of central nervous system and other disorders.

5 Claims, No Drawings

2-AMINO-6-(2,4,5-SUBSTITUTED-PHENYL)-PYRIDINES

CROSS REFERENCE TO RELATED APPLICATIONS

The present application claims benefit of U.S. Provisional Application Ser. Nos. 60/328,252 and 60/328,253, both filed on Oct. 10, 2001.

The present invention relates to certain 2-amino-6-(2,4,5-substituted-phenyl)-pyridines, to pharmaceutical compositions containing them and to their use in the treatment and prevention of central nervous system and other disorders The compounds of this invention exhibit activity as nitric oxide synthase (NOS) inhibitors.

There are three known isoforms of NOS—an inducible form (I-NOS) and two constitutive forms referred to as, respectively, neuronal NOS (N-NOS) and endothelial NOS (E-NOS). Each of these enzymes carries out the conversion of arginine to citrulline while producing a molecule of nitric oxide (NO) in response to various stimuli. It is believed that excess nitric oxide (NO) production by NOS plays a role in the pathology of a number of disorders and conditions in mammals. For example, NO produced by I-NOS is thought to play a role in diseases that involve systemic hypotension such as toxic shock and therapy with certain cytokines. It has been shown that cancer patients treated with cytokines such as interleukin 1 (IL-1), interleukin 2 (IL-2) or tumor necrosis factor (TNF) suffer cytokine-induced shock and hypotension due to NO produced from macrophages, i.e., inducible NOS (I-NOS), see *Chemical & Engineering News*, December 20, p. 33, (1993). I-NOS inhibitors can reverse this. It is also believed that I-NOS plays a role in the pathology of diseases of the central nervous system such as ischemia. For example, inhibition of I-NOS has been shown to ameliorate cerebral ischemic damage in rats, see *Am. J. Physiol.*, 268, p. R286 (1995)). Suppression of adjuvant induced arthritis by selective inhibition of I-NOS is reported in *Eur. J. Pharmacol.*, 273, p. 15–24 (1995).

NO produced by N-NOS is thought to play a role in diseases such as cerebral ischemia, pain, and opiate tolerance. For example, inhibition of N-NOS decreases infarct volume after proximal middle cerebral artery occlusion in the rat, see *J. Cerebr. Blood Flow Metab.*, 14, p. 924–929 (1994). N-NOS inhibition has also been shown to be effective in antinociception, as evidenced by activity in the late phase of the formalin-induced hindpaw licking and acetic acid-induced abdominal constriction assays, see *Br. J. Pharmacol.*, 110, p. 219–224 (1993). Finally, opioid withdrawal in rodents has been reported to be reduced by N-NOS inhibition, see *Neuropsychopharmacol.*, 13, p. 269–293 (1995).

Other NOS inhibitors and their utility as pharmaceutical agents in the treatment of central nervous system disorders and other disorders are referred to in the following references: U.S. patent application Ser. No. 09/325,480, filed Jun. 3, 1999, allowed Nov. 14, 2000, U.S. patent application Ser. No. 09/802,086, filed Mar. 8, 2001, and counterpart International Patent Application No. WO 98/24766, published Jun. 11, 1998; U.S. Pat. No. 6,235,747, issued May 22, 2001, U.S. patent application Ser. No. 09/826,132, filed Apr. 4, 2001, and counterpart International Patent Application No. WO 97/36871, published Oct. 9, 1997; U.S. patent application Ser. No. 09/740,385, filed Dec. 20, 2000, and counterpart International Patent Application No. WO 99/10339, published Mar. 4, 1999; U.S. patent application Ser. No. 09/381,887, filed Mar. 28, 2000, and counterpart International Patent Application No. WO 99/11620, published Mar. 11, 1999; U.S. patent application Ser. No. 09/127,158, filed Jul. 31, 1998, and counterpart International Patent Application No. WO 98/34919, published Aug. 13, 1998; and U.S. patent application Ser. No. 09/403,177, filed Oct. 18, 1999, and counterpart International Patent Application No. WO 99/62883, published Dec. 9, 1999.

SUMMARY OF THE INVENTION

The present invention relates to a compound, or pharmaceutically acceptable salt thereof, that is selected from the following compounds and their pharmaceutically acceptable salts:

(a) 6-[4-(N-methyl-3-azetidinoxy)-5-ethyl-2-methoxyphenyl]-pyridin-2-ylamine, which has the following structure

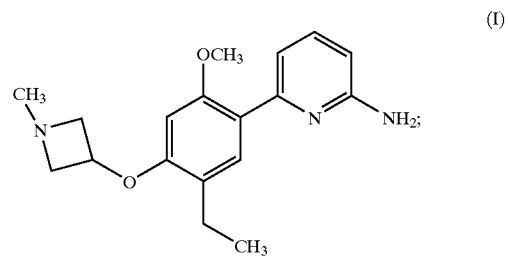

(b) 6-[4-(N,N-dimethylaminomethyl)-5-ethyl-2-methoxy-phenyl]-pyridin-2-ylamine, which has the following structure

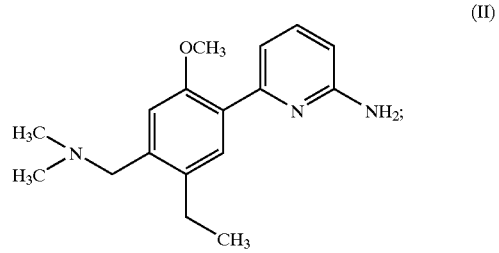

(c) 6-[4-(N-methylaminomethyl)-5-ethyl-2-methoxyphenyl]-pyridin-2-ylamine, which has the following structure

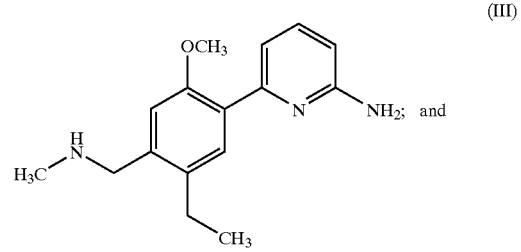

(d) 6-[4-(3-azetidinoxy)-5-ethyl-2-methoxy-phenyl]-pyridin-2-ylamine, which has the following structure

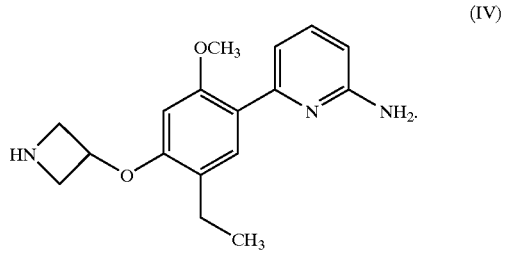

(IV)

In so far as the compounds of formulas I, II, III and IV of this invention contain basic groups, they can form acid addition salts with various inorganic and organic acids. The present invention also relates to the pharmaceutically acceptable acid addition salts of compounds of the formulas I, II, III and IV. Although such salts must be pharmaceutically acceptable for administration to animals, it is often desirable in practice to initially isolate the base compound from the reaction mixture as a pharmaceutically unacceptable salt and then simply convert to the free base compound by treatment with an alkaline reagent, and thereafter, convert the free base to a pharmaceutically acceptable acid addition salt. The acid addition salts of the base compounds of this invention are readily prepared by treating the base compound with a substantially equivalent amount of the chosen mineral or organic acid in an aqueous solvent or in a suitable organic solvent, such as methanol or ethanol. Upon careful evaporation of the solvent, the desired solid salt is readily obtained. The acids which are used to prepare the pharmaceutically acceptable acid addition salts of the aforementioned base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, p-toluenesulfonate and pamoate (i.e., 1,1'-methylene-bis-(2-hydroxy-3-naphthoate))salts.

The present invention also includes isotopically-labeled compounds that are identical to those recited in formulas I, II, III and IV, but for the fact that one or more atoms are replaced by an atom having an atomic mass or mass number different from the atomic mass or mass number usually found in nature. Examples of isotopes that can be incorporated into the compounds of the present invention include isotopes of hydrogen, carbon, nitrogen and oxygen, such as $^2H$, $^3H$, $^{13}C$, $^{11}C$, $^{14}C$, $^{15}N$, $^{18}O$, $^{17}O$, respectively. The compounds of the present invention, prodrugs thereof, and pharmaceutically acceptable salts of such compounds or of such prodrugs which contain the aforementioned isotopes and/or other isotopes are within the scope of this invention. Such compounds may be useful as research and diagnostic tools in metabolism pharmacokinetic studies and in binding assays. Certain isotopically-labeled compounds of the present invention, for example, those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically-labeled compounds of the present invention and prodrugs thereof can generally be prepared by carrying out the procedures disclosed in the schemes and discussion of the schemes and/or in the examples and preparations described herein, by substituting a readily available isotopically-labeled reagent for a nonisotopically-labeled reagent.

More specific embodiments of this invention relate to a compound of the formula I, which has the chemical name 6-[4-(N-methyl-3-azetidinoxy)-5-ethyl-2-methoxy-phenyl]-pyridin-2-ylamine, and the pharmaceutically acceptable salts of such compound.

Other more specific embodiments of this invention relate to a compound of the formula II, which has the chemical name 6-[4-(N,N-dimethylaminomethyl)-5-ethyl-2-methoxy-phenyl]-pyridin-2-ylamine, and the pharmaceutically acceptable salts of such compound.

Other more specific embodiments of this invention relate to a compound of the formula III, which has the chemical name 6-[4-(N-methylaminomethyl)-5-ethyl-2-methoxy-phenyl]-pyridin-2-ylamine, and the pharmaceutically acceptable salts of such compound.

Other more specific embodiments of this invention relate to a compound of the formula IV, which has the chemical name 6-[4-(3-azetidinoxy)-5-ethyl-2-methoxy-phenyl]-pyridin-2-ylamine, and the pharmaceutically acceptable salts of such compound.

The compounds of formulas I, II, III and IV of this invention, and their pharmaceutically acceptable salts, have useful pharmaceutical and medicinal properties. The compounds of formulas I, II, III and IV, and their pharmaceutically acceptable salts, are useful as NOS inhibitors i.e., they possess the ability to inhibit the NOS enzyme in mammals, and therefore they are able to function as therapeutic agents in the treatment of the disorders and diseases enumerated below in an afflicted mammal.

The term "treating," as used herein, refers to reversing, alleviating, or inhibiting the progress of the disease, disorder or condition, or one or more symptoms of such disease, disorder or condition, to which such term applies. Depending on the condition of the patient, as used herein, this term also refers to preventing a disease, disorder or condition, and includes preventing the onset of a disease, disorder or condition, or preventing the symptoms associated with a disease, disorder or condition. As used herein, this term also refers to reducing the severity of a disease, disorder or condition or symptoms associated with such disease, disorder or condition prior to affliction with the disease, disorder or condition. Such prevention or reduction of the severity of a disease, disorder or condition prior to affliction refers to administration of the composition of the present invention, as described herein, to a subject that is not at the time of administration afflicted with the disease, disorder or condition. "Preventing" also refers to preventing the recurrence of a disease, disorder or condition or of one or more symptoms associated with such disease, disorder or condition. The terms "treatment" and "therapeutically," as used herein, refer to the act of treating, as "treating" is defined above.

The present invention also relates to a pharmaceutical composition for treating a condition selected from the group consisting of migraine, inflammatory diseases (e.g., asthma, psoriasis, eczema, arthritis), stroke, acute, chronic and neuropathic pain, hypovolemic shock, traumatic shock, reperfusion injury, Crohn's disease, ulcerative colitis, septic shock, multiple sclerosis, AIDS associated dementia, neurodegenerative diseases, neuron toxicity, Alzheimer's disease, chemical dependencies and addiction (e.g., dependencies on drugs, alcohol and nicotine), emesis, epilepsy, anxiety, psychosis, head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spinal cord injury, Huntington's disease, Parkinson's disease, glaucoma, macular degeneration, diabetic neuropathy, diabetic nephropathy and cancer in a mammal, including a human, comprising an amount of a compound of the formula I, II, III or IV, or a pharmaceutically acceptable salt thereof, that is effective in treating such condition, and a pharmaceutically acceptable carrier.

This invention also relates to the above pharmaceutical composition for treating a condition selected from the group of conditions referred to above, in a mammal, including a human, comprising an amount of a compound of the formula I, or a pharmaceutically acceptable salt thereof, that is effective in treating such condition, and a pharmaceutically acceptable carrier.

This invention also relates to the above pharmaceutical composition for treating a condition selected from the group of conditions referred to above, in a mammal, including a human, comprising an amount of a compound of the formula II, or a pharmaceutically acceptable salt thereof, that is effective in treating such condition, and a pharmaceutically acceptable carrier.

This invention also relates to the above pharmaceutical composition for treating a condition selected from the group of conditions referred to above, in a mammal, including a human, comprising an amount of a compound of the formula III, or a pharmaceutically acceptable salt thereof, that is effective in treating such condition, and a pharmaceutically acceptable carrier.

This invention also relates to the above pharmaceutical composition for treating a condition selected from the group of conditions referred to above, in a mammal, including a human, comprising an amount of a compound of the formula IV, or a pharmaceutically acceptable salt thereof, that is effective in treating such condition, and a pharmaceutically acceptable carrier.

The present invention also relates to a method of treating a condition selected from the group consisting of migraine, inflammatory diseases (e.g., asthma, psoriasis, eczema, arthritis), stroke, acute, chronic and neuropathic pain, hypovolemic shock, traumatic shock, reperfusion injury, Crohn's disease, ulcerative colitis, septic shock, multiple sclerosis, AIDS associated dementia, neurodegenerative diseases, neuron toxicity, Alzheimer's disease, chemical dependencies and addictions (e.g., dependencies on drugs, alcohol and nicotine), emesis, epilepsy, anxiety, psychosis, head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spinal cord injury, Huntington's disease, Parkinson's disease, glaucoma, macular degeneration, diabetic neuropathy, diabetic nephropathy and cancer in a mammal, including a human, comprising administering to said mammal an amount of a compound of the formula I, II, III or IV, or a pharmaceutically acceptable salt thereof, that is effective in treating such condition.

This invention also relates to the above method of treating a condition selected from the group of conditions referred to above, in a mammal, including a human, comprising administering to said mammal an amount of a compound of the formula I, or a pharmaceutically acceptable salt thereof, that is effective in treating such condition.

This invention also relates to the above method of treating a condition selected from the group of conditions referred to above, in a mammal, including a human, comprising administering to said mammal an amount of a compound of the formula II, or a pharmaceutically acceptable salt thereof, that is effective in treating such condition.

This invention also relates to the above method of treating a condition selected from the group of conditions referred to above, in a mammal, including a human, comprising administering to said mammal an amount of a compound of the formula III, or a pharmaceutically acceptable salt thereof, that is effective in treating such condition.

This invention also relates to the above method of treating a condition selected from the group of conditions referred to above, in a mammal, including a human, comprising administering to said mammal an amount of a compound of the formula IV, or a pharmaceutically acceptable salt thereof, that is effective in treating such condition.

The present invention also relates to a pharmaceutical composition for inhibiting nitric oxide synthase (NOS) in a mammal, including a human, comprising a NOS inhibiting effective amount of a compound of the formula I, II, III or IV, or a pharmaceutically acceptable salt thereof, and a pharmaceutically acceptable carrier.

This invention also relates to the above pharmaceutical composition for inhibiting NOS in a mammal, including a human, comprising a NOS inhibiting effective amount of a compound of the formula I, or a pharmaceutically acceptable salt thereof, and a pharmaceutically acceptable carrier.

This invention also relates to the above pharmaceutical composition for inhibiting NOS in a mammal, including a human, comprising a NOS inhibiting effective amount of a compound of the formula II, or a pharmaceutically acceptable salt thereof, and a pharmaceutically acceptable carrier.

This invention also relates to the above pharmaceutical composition for inhibiting NOS in a mammal, including a human, comprising a NOS inhibiting effective amount of a compound of the formula III, or a pharmaceutically acceptable salt thereof, and a pharmaceutically acceptable carrier.

This invention also relates to the above pharmaceutical composition for inhibiting NOS in a mammal, including a human, comprising a NOS inhibiting effective amount of a compound of the formula IV, or a pharmaceutically acceptable salt thereof, and a pharmaceutically acceptable carrier.

The present invention also relates to a method of inhibiting NOS in a mammal, including a human, comprising administering to said mammal a NOS inhibiting effective amount of a compound of the formula I, II, III or IV, or a pharmaceutically acceptable salt thereof.

This invention also relates to the above method of inhibiting NOS in a mammal, including a human, comprising administering to said mammal a NOS inhibiting effective amount of a compound of the formula I, or a pharmaceutically acceptable salt thereof.

This invention also relates to the above method of inhibiting NOS in a mammal, including a human, comprising administering to said mammal a NOS inhibiting effective amount of a compound of the formula II, or a pharmaceutically acceptable salt thereof.

This invention also relates to the above method of inhibiting NOS in a mammal, including a human, comprising administering to said mammal a NOS inhibiting effective amount of a compound of the formula III, or a pharmaceutically acceptable salt thereof.

This invention also relates to the above method of inhibiting NOS in a mammal, including a human, comprising administering to said mammal a NOS inhibiting effective amount of a compound of the formula IV, or a pharmaceutically acceptable salt thereof.

The present invention also relates to a pharmaceutical composition for treating a condition selected from the group consisting of migraine, inflammatory diseases (e.g., asthma, psoriasis, arthritis, eczema), stroke, acute, chronic and neuropathic pain, hypovolemic shock, traumatic shock, reperfusion injury, Crohn's disease, ulcerative colitis, septic shock, multiple sclerosis, AIDS associated dementia, neurodegenerative diseases, neuron toxicity, Alzheimer's disease, chemical dependencies and addictions (e.g., dependencies on drugs, alcohol and nicotine), emesis, epilepsy, anxiety, psychosis, head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spinal cord injury, Huntington's disease, glaucoma, macular degeneration, diabetic neuropathy, diabetic nephropathy and cancer in a mammal, including a human, comprising a NOS inhibiting effective amount of a compound of the formula I, II, III or IV, or a pharmaceutically acceptable salt thereof, and a pharmaceutically acceptable carrier.

This invention also relates to the above pharmaceutical composition for treating a condition selected from the group of conditions referred to above, in a mammal, including a human, comprising a NOS inhibiting effective amount of a compound of the formula I, or a pharmaceutically acceptable salt thereof, and a pharmaceutically acceptable carrier.

This invention also relates to the above pharmaceutical composition for treating a condition selected from the group of conditions referred to above, in a mammal, including a human, comprising a NOS inhibiting effective amount of a compound of the formula II, or a pharmaceutically acceptable salt thereof, and a pharmaceutically acceptable carrier.

This invention also relates to the above pharmaceutical composition for treating a condition selected from the group of conditions referred to above, in a mammal, including a human, comprising a NOS inhibiting effective amount of a compound of the formula III, or a pharmaceutically acceptable salt thereof, and a pharmaceutically acceptable carrier.

This invention also relates to the above pharmaceutical composition for treating a condition selected from the group of conditions referred to above, in a mammal, including a human, comprising a NOS inhibiting effective amount of a compound of the formula IV, or a pharmaceutically acceptable salt thereof, and a pharmaceutically acceptable carrier.

The present invention also relates to a method of treating a condition selected from the group consisting of migraine, inflammatory diseases (e.g., asthma, psoriasis, eczema, arthritis), stroke, acute, chronic and neuropathic pain, hypovolemic shock, traumatic shock, reperfusion injury, Crohn's disease, ulcerative colitis, septic shock, multiple sclerosis, AIDS associated dementia, neurodegenerative diseases, neuron toxicity, Alzheimer's disease, chemical dependencies and addictions (e.g., dependencies on drugs, alcohol or nicotine), emesis, epilepsy, anxiety, psychosis, head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spinal cord injury, Huntington's disease, Parkinson's disease, glaucoma, macular degeneration, diabetic neuropathy, diabetic nephropathy and cancer in a mammal, including a human, comprising administering to said mammal a NOS inhibiting effective amount of a compound of the formula I, II, III or IV, or a pharmaceutically acceptable salt thereof.

This invention also relates to the above method of treating a condition selected from the group of conditions referred to above, in a mammal, including a human, comprising administering to said mammal a NOS inhibiting effective amount of a compound of the formula I, or a pharmaceutically acceptable salt thereof.

This invention also relates to the above method of treating a condition selected from the group of conditions referred to above, in a mammal, including a human, comprising administering to said mammal a NOS inhibiting effective amount of a compound of the formula II, or a pharmaceutically acceptable salt thereof.

This invention also relates to the above method of treating a condition selected from the group of conditions referred to above, in a mammal, including a human, comprising administering to said mammal a NOS inhibiting effective amount of a compound of the formula III, or a pharmaceutically acceptable salt thereof.

This invention also relates to the above method of treating a condition selected from the group of conditions referred to above, in a mammal, including a human, comprising administering to said mammal a NOS inhibiting effective amount of a compound of the formula IV, or a pharmaceutically acceptable salt thereof.

DETAILED DESCRIPTION OF THE INVENTION

In the reaction schemes and discussion that follow, formulas I, II, III and IV are defined as set forth above in the Summary of the Invention.

Compounds of the formulas I and IV, and their pharmaceutically acceptable salts, may be prepared as described in the following reaction schemes and discussion, and as described in U.S. patent application Ser. No. 09/127,158, filed Jul. 31, 1998, entitled 2-Amino-6-(2-substituted-4-phenoxy)-substituted-pyridines, and counterpart International Patent Application No. WO 98/34919, published Aug. 13, 1998. The foregoing patent applications are incorporated herein by reference in their entirety.

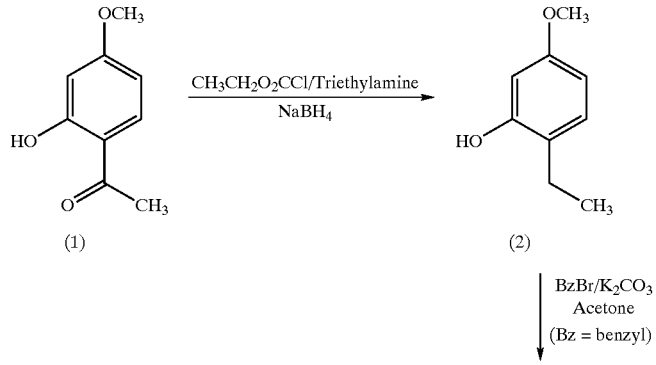

-continued
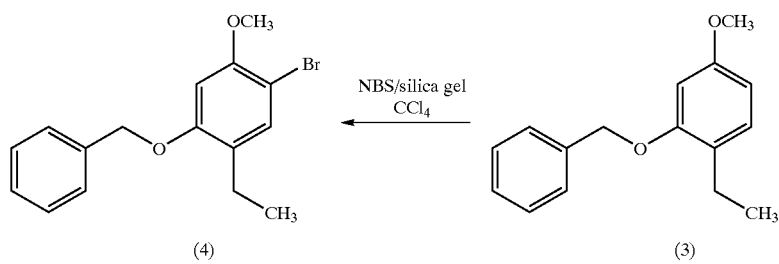
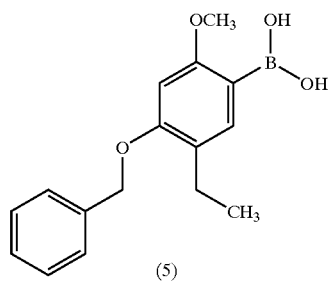
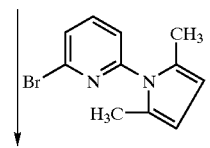
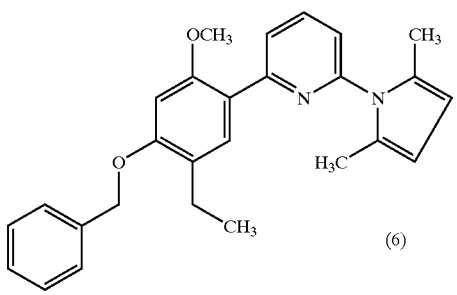
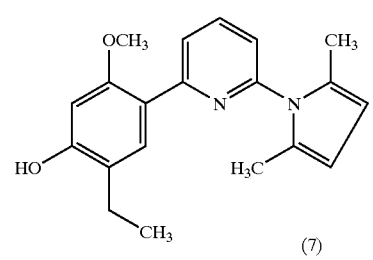

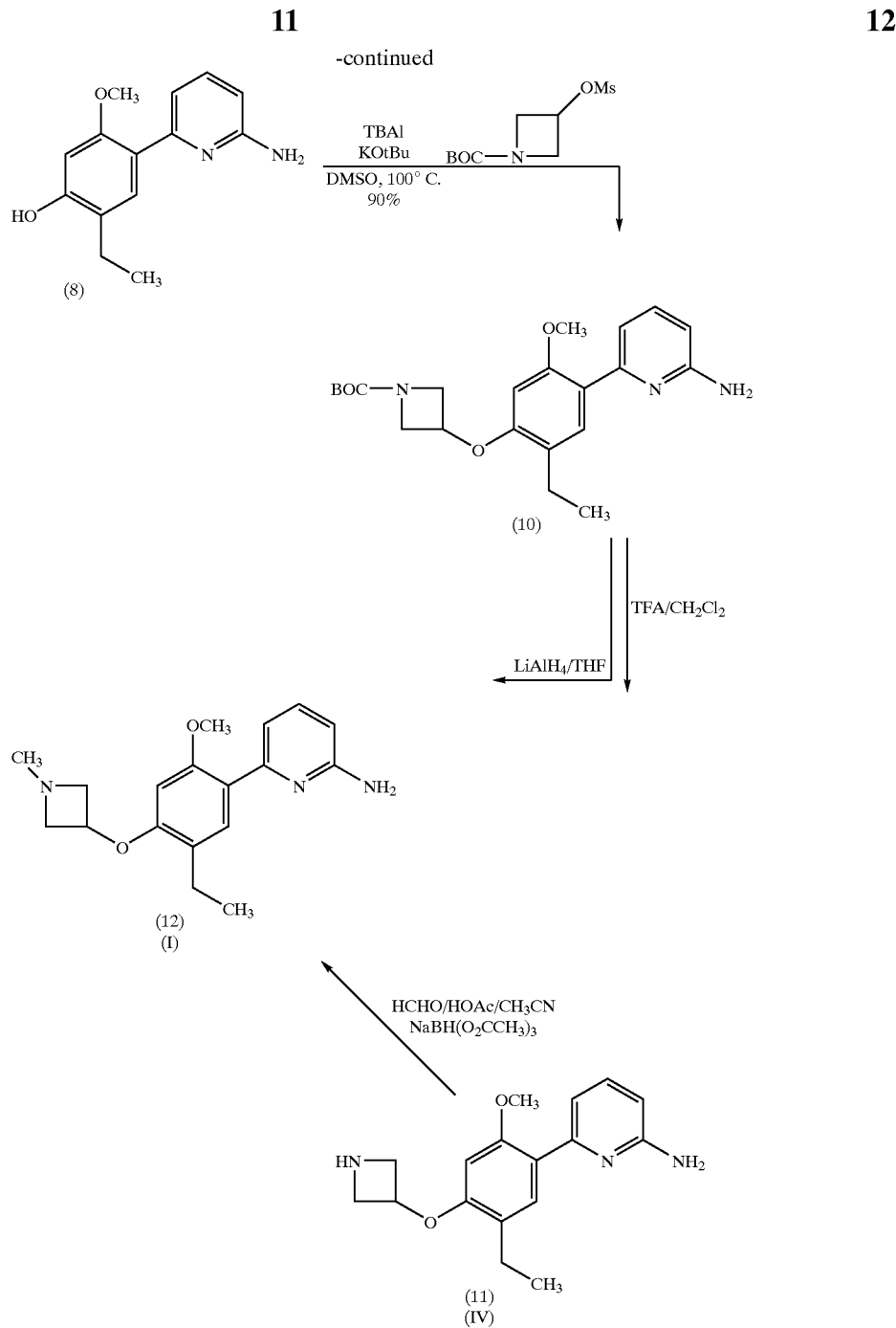

Scheme 1 illustrates a method for preparing the compound 6-[4-(N-methyl-3-azetidinoxy)-5-ethyl-2-methoxy-phenyl]-pyridin-2-ylamine, the compound of the formula I, and 6-[4-(3-azetidinoxy)-5-ethyl-2-methoxy-phenyl]-pyridin-2-ylamine, the compound of the formula II. These compounds are referred to in Scheme 1 as compounds of the formula "(I)" (or "(12)") and "(IV)" (or "(11)"), respectively.

The following reactions, which are illustrated in Scheme 1, are preferably conducted under a nitrogen atmosphere (unless otherwise indicated).

Referring to Scheme 1, 2-acetyl-5-methoxyphenol (1) may be reduced to 2-ethyl-5-methoxyphenol (2) by the methods described in *Chem. Pharm. Bull.* (Japan), 27 (1979) 1490–94. For example, 2-acetyl-5-methoxyphenol (1) can be treated with a reducing agent such as sodium borohydride in tetrahydrofuran (THF) along with a base such as triethylamine and an acylating agent such as ethyl chloroformate. Other tertiary amines and chloroformates can be used. While THF is the preferred solvent, diethyl ether can also be used. This reaction can be carried out at a temperature from about 0° C. to about 10° C., preferably about 0° C.

The alcohol group in the 2-ethyl-5-methoxyphenol (2) is protected by conversion to 3-benzyloxy-4-ethyl-1-methoxybenzene (3). More specifically 2-ethyl-5-methoxyphenol (2) is allowed to react with benzyl bromide and potassium carbonate in a polar solvent such as acetonitrile, dimethylformamide (DMF) or acetone, preferably acetone. The reaction yields 3-benzyloxy-4-ethyl-1-methoxybenzene (3). This reaction can be carried out at a temperature from about room temperature to about 60° C., preferably about 60° C.

Alternatively, 2-ethyl-5-methoxyphenol (2) may be allowed to react with benzyl bromide and potassium hydroxide in a polar solvent such as acetonitrile, dimethylsulfoxide (DMSO) or dimethylformamide (DMF), preferably acetonitrile. In this alternative reaction, a catalyst such as dibenzo-18-crown-6 may be used. This reaction also yields 3-benzyloxy-4-ethyl-1-methoxybenzene (3). The reaction is generally carried out at a temperature from about room temperature to about the reflux temperature of the reaction mixture, preferably at about the reflux temperature of the reaction mixture.

In a bromination reaction, the 3-benzyloxy-4-ethyl-1-methoxybenzene (3) is combined with N-bromosuccinimide (NBS) and silica gel 60 (EM Science, 480 Democrat Road, Gibbstown, N.J. 08027, an affiliate of Merck KGaA, Darmstadt, Germany) in a nonpolar solvent such as carbon tetrachloride at a temperature from about 0° C. to about room temperature. Preferably, the reaction is conducted at about room temperature. This reaction is allowed to stir, in the absence of light, to yield 5-benzyloxy-2-bromo-4-ethyl-1-methoxybenzene (4).

The resulting 5-benzyloxy-2-bromo-4-ethyl-1-methoxybenzene (4) is allowed to react with n-butyl lithium in a polar solvent such as ether, glyme or tetrahydrofuran (THF), preferably THF, at a temperature of about −78° C. Triethyl borate is then added to the reaction mixture, and the reaction mixture is allowed to stir at a temperature of about −78° C. The reaction mixture is then allowed to warm to about room temperature. The reaction yields 4-benzyloxy-5-ethyl-2-methoxy-phenylboronic acid (5).

Reacting the 4-benzyloxy-5-ethyl-2-methoxy-phenylboronic acid (5) with 2-bromo-6-(2,5-dimethylpyrrol-1-yl)pyridine, sodium carbonate and tetrakis(triphenylphosphine)palladium(0) in a polar solvent such as methanol/water, ethanol/water, or tetrahydrofuran (THF)/water, preferably ethanol/water, at a temperature from about room temperature to about the reflux temperature of the reaction mixture, preferably at about the reflux temperature, yields 2-(4-benzyloxy-5-ethyl-2-methoxy-phenyl)-6-(2,5-dimethyl-pyrrol-1-yl)-pyridine (6).

Alternatively, the 2-bromo-6-(2,5-dimethylpyrrol-1-yl) pyridine in the above reaction may be replaced with a compound having the structural formula

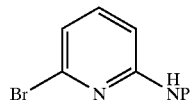

wherein P is a nitrogen protecting group such as trimethylacetyl or another appropriate nitrogen protecting group. Such protecting groups are well known to those of skill in the art. For example, nitrogen protecting groups are discussed in Greene, Theodora W. and Wuts, Peter G. M., *Protective Groups In Organic Synthesis*, Second Edition, John Wiley & Sons, Inc., New York, 1991 at pages 309–405. The above compounds are either commercially available, known in the scientific literature or easily obtained using well known methods and reagents.

The benzyl protecting group can be removed from the 2-(4-benzyloxy-5-ethyl-2-methoxy-phenyl)-6-(2,5-dimethyl-pyrrol-1-yl)-pyridine (6) by reacting this compound with ammonium formate in a polar solvent such as water or a lower alcohol solvent (e.g., methanol or ethanol), or in a mixture of one or more of these solvents, preferably methanol, at a temperature from about room temperature to about the reflux temperature of the reaction mixture. This reaction is preferably carried out at about the reflux temperature in the presence of about 20% palladium hydroxide on carbon. The aminopyridine protecting group is then removed from the resulting 4-[6-(2,5-dimethyl-pyrrol-1-yl)-pyridin-2-yl]-6-ethyl-3-methoxyphenol (7) in a conversion to 4-(6-amino-pyridin-2-yl)-2-ethyl-5-methoxyphenol (8). The 4-[6-(2,5-dimethyl-pyrrol-1-yl)-pyridin-2-yl]-6-ethyl-3-methoxyphenol (7) is converted to 4-(6-amino-pyridin-2-yl)-2-ethyl-5-methoxyphenol (8) by reacting it with hydroxylamine in a polar solvent such as water, a lower alcohol, such as methanol or ethanol, or a mixture of these solvents, preferably methanol/water. This reaction is conducted at a temperature from about room temperature to about the reflux temperature of the solvent, preferably at about the reflux temperature.

The 4-(6-amino-pyridin-2-yl)-2-ethyl-5-methoxyphenol (8) is treated with potassium t-butoxide and allowed to react with 3-methanesulfonyloxy-azetidine-1-carboxylic acid tert-butyl ester in a polar solvent such as dimethylsulfoxide (DMSO), dimethylformamide (DMF) or 1-methyl-2-pyrrolidinone, preferably DMSO, to form 6-[4-(3-azetidinoxy-1-carboxylic acid tert-butyl ester)-5-ethyl-2-methoxy-phenyl]-pyridin-2-ylamine (10). Other nitrogen protecting groups such as —C(═O)OCH$_2$C$_6$H$_5$, trifluoroacetyl and COOR (wherein R is benzyl, phenyl, alkyl, formyl or a similar group) can be used to protect the azetidine nitrogen. In addition, the mesylate leaving group can be replaced with another appropriate leaving group such as tosylate, trifluoroacetate or triflate. Other bases such as lithium t-butoxide can also be used. Preferably, a catalytic amount of tetrabutylammonium iodide (TBAI) is added to the reaction mixture. Other catalysts such as tetrabenzylammonium iodide and benzyltrimethylammonium iodide may also be used. This alkylation reaction is typically carried out in the presence of an alkali metal alkoxide such as lithium or potassium tert-butoxide, preferably potassium tert-butoxide, in a high boiling polar organic solvent such as DMSO, DMF or 1-methyl-2-pyrrolidinone, preferably DMSO. The reaction temperature can range from about 50° C. to about 100° C., and is preferably about 100° C.

Alternatively, 4-(6-amino-pyridin-2-yl)-2-ethyl-5-methoxyphenol (8) may be reacted with a compound having the structural formula

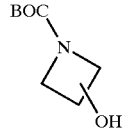

using triphenylphosphine and diethylazodicarboxylate or a water soluble azodicarboxylate in tetrahydrofuran (THF) under standard Mitsunobo reaction conditions to yield 6-[4-(3-azetidinoxy-1-carboxylic acid tert-butyl ester)-5-ethyl-2-methoxy-phenyl]-pyridin-2-ylamine (10). Typically, the reactants are combined at about 0° C. and then allowed to warm to room temperature.

Reduction of the 6-[4-(3-azetidinoxy-1-carboxylic acid tert-butyl ester)-5-ethyl-2-methoxy-phenyl]-pyridin-2-ylamine (10) yields the compound of formula I, 6-[4-(N-methyl-3-azetidinoxy)-5-ethyl-2-methoxy-phenyl]-pyridin-2-ylamine (12). This reduction is preferably accomplished using lithium aluminum hydride as the reducing agent and tetrahydrofuran (THF) or another organic ether (e.g., ethyl ether or glyme) as the solvent. Other aluminum hydride reducing agents can also be used, such as diisobutyl aluminum hydride. Diborane can also be used as the reducing agent. The foregoing reaction is generally conducted at a temperature from about room temperature to about the reflux temperature of the reaction mixture, preferably at about the reflux temperature.

Alternatively, the 6-[4-(3-azetidinoxy-1-carboxylic acid tert-butyl ester)-5-ethyl-2-methoxy-phenyl]-pyridin-2-ylamine (10) may be deprotected to yield the compound of formula IV, (6-[4-(3-azetidinoxy)-5-ethyl-2-methoxy-phenyl]-pyridin-2-ylamine (11). This transformation is preferably accomplished using trifluoroacetic acid (TFA) as the acid catalyst, either neat or in a polar solvent such as dichloromethane, chloroform or dichloroethane, preferably dichloromethane. Other acid catalysts can also be used, such as hydrochloric acid, hydrobromic acid or toluenesulfonic acid. This reaction is generally conducted at a temperature from about 0° C. to about room temperature, preferably at about room temperature.

The compound of formula IV, 6-[4-(3-azetidinoxy)-5-ethyl-2-methoxy-phenyl]-pyridin-2-ylamine (11), may itself be converted to the compound of formula I, 6-[4-(N-methyl-3-azetidinoxy)-5-ethyl-2-methoxy-phenyl]-pyridin-2-ylamine (12), by reductive amination. This reductive amination is preferably accomplished using formaldehyde, acetic acid and sodium triacetoxy borohydride as the reducing agent and acetonitrile/water, dichloromethane or methanol, preferably acetonitrile/water, as the solvent. Other reducing agents can also be used, such as sodium cyanoborohydride. The above reaction is generally conducted at a temperature from about 0° C. to about room temperature, preferably at about room temperature.

The starting materials used in the procedures of Scheme 1, the syntheses of which are not described above, are either commercially available, known in the art or readily obtainable from known compounds using methods that will be apparent to those skilled in the art.

The compounds of formulas I and IV, and the intermediates shown in the above reaction schemes, can be isolated and purified by conventional procedures, such as recrystallization or chromatographic separation.

Compounds of the formulas II and III, and their pharmaceutically acceptable salts, may be prepared as described in the following reaction schemes and discussion.

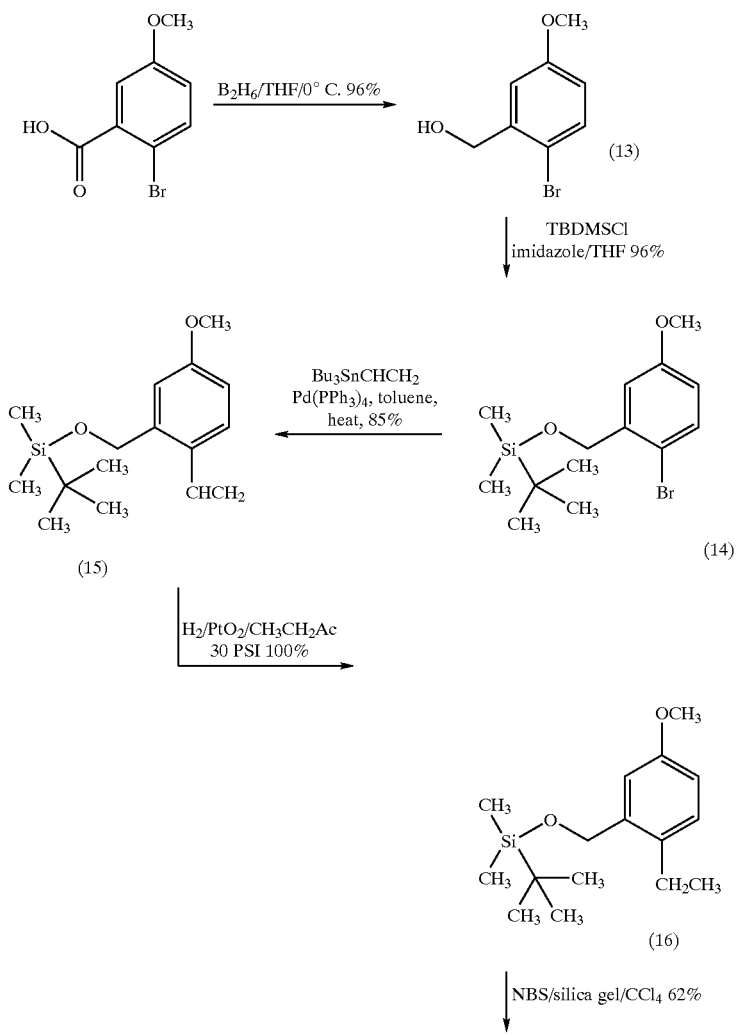

Scheme 2

-continued
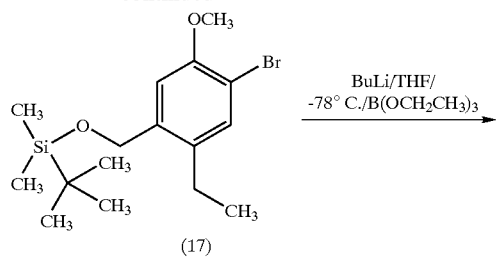
(17)
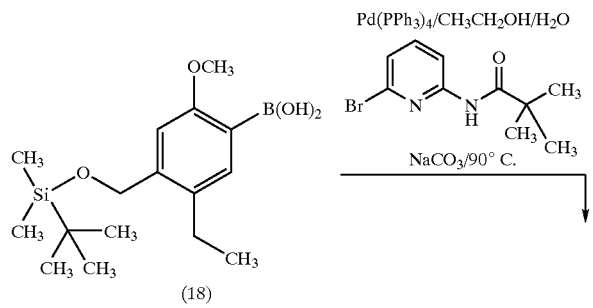
(18)
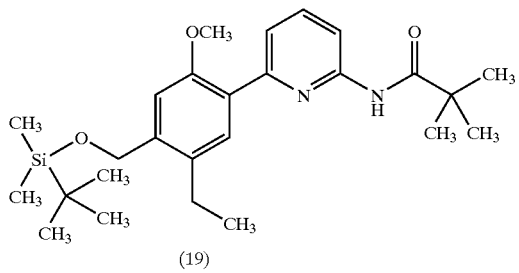
(19)
TBAF/THF 45%(2 steps)
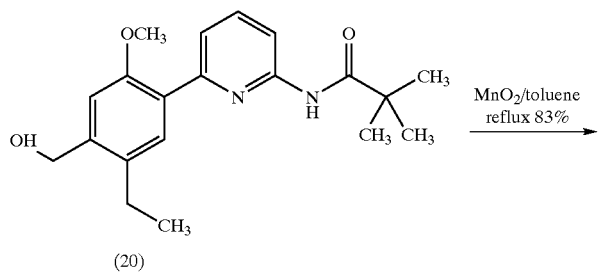
(20)
MnO₂/toluene
reflux 83%
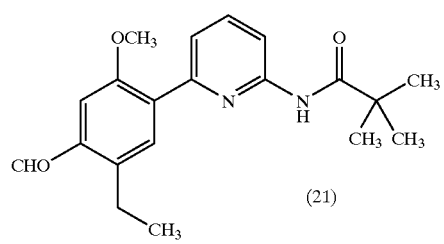
(21)

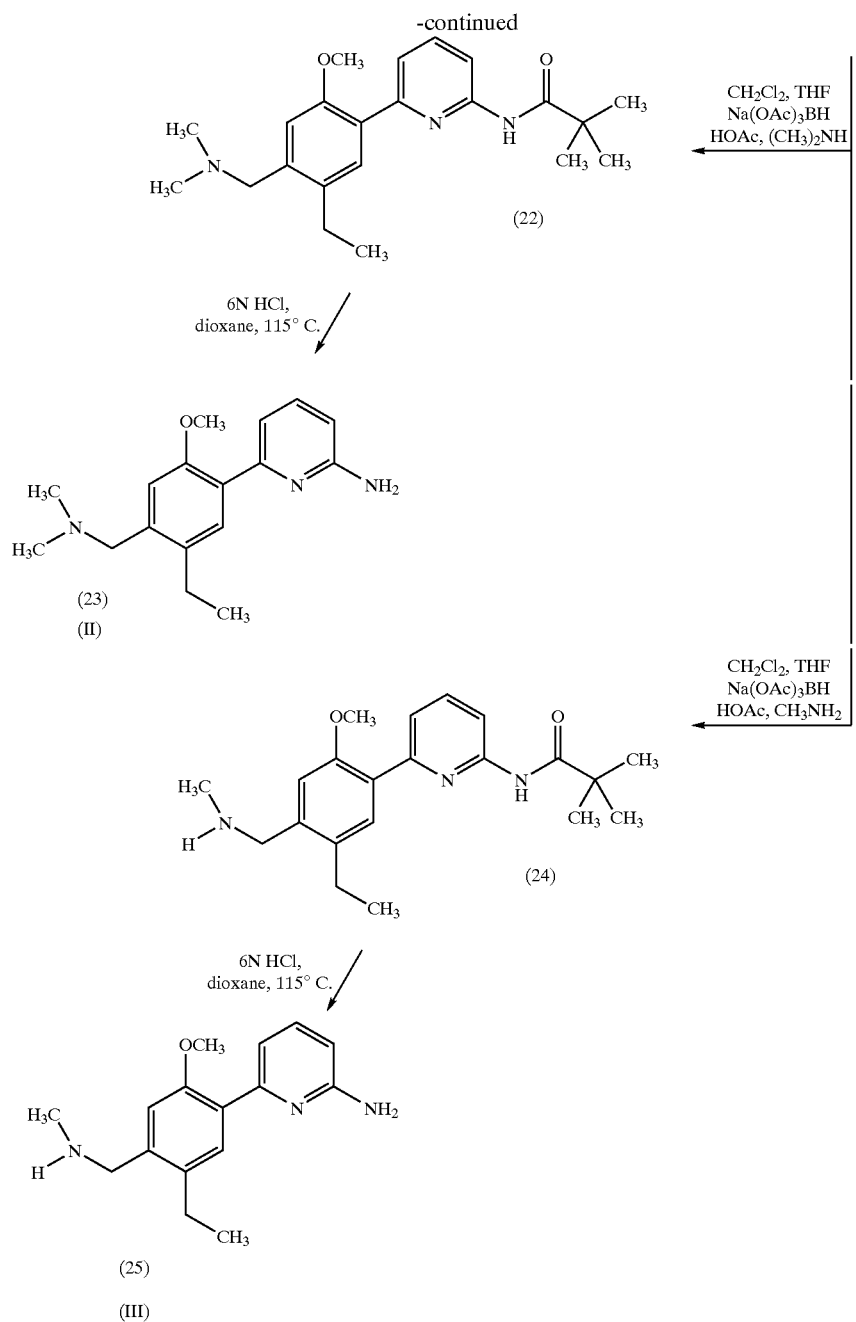

Scheme 2 illustrates a method for preparing the compound 6-[4-(N,N-dimethylaminomethyl)-5-ethyl-2-methoxy-phenyl]-pyridin-2-ylamine, the compound of the formula II, and 6-[4-(N-methylaminomethyl)-5-ethyl-2-methoxy-phenyl]-pyridin-2-ylamine, the compound of the formula III. These compounds are referred to in Scheme 2 as compounds of the formulas "(II)" (or "(23)") and "(III)" (or "(25)"), respectively.

The following reactions, which are illustrated in Scheme 2, are preferably conducted under a nitrogen atmosphere (unless otherwise indicated).

Referring to Scheme 2, 2-bromo-5-methoxybenzoic acid is reduced to 2-bromo-5-methoxybenzyl alcohol (13) using borane (1 M in tetrahydrofuran (THF)) in a solvent such as THF, diethyl ether or diglyme, preferably THF. Other suitable reducing agents that may be used in the above transformation include $BH_3.SMe_2$ and lithium aluminum hydride/aluminum chloride. The reduction may be carried out at a temperature from about 0° C. to about room temperature, preferably about 0° C.

The alcohol group in the 2-bromo-5-methoxybenzyl alcohol (13) is protected by conversion to 2-bromo-5-methoxy-benzyloxy)-tert-butyl-dimethyl-silane (14). More specifically, 2-bromo-5-methoxybenzyl alcohol (13) is converted to 2-bromo-5-methoxy-benzyloxy)-tert-butyl-dimethyl-silane (14) with imidazole and t-butyl dimethylsilylchloride(TBDMSCl), or $TBDMSOSO_2CF_3$, in a solvent such as tetrahydrofuran (THF), dimethylformamide (DMF) or methylene chloride, preferably anhydrous THF, at a temperature from about 0° C. to about room temperature, preferably about room temperature.

In a Stille coupling reaction, 2-bromo-5-methoxy-benzyloxy)-tert-butyl-dimethyl-silane (14) is converted to tert-butyl-dimethyl-(2-vinyl-5-methoxy-benzyloxy)-silane (15). The conversion is carried out using tributylvinyl tin in a solvent such as toluene, dimethylformamide (DMF), acetone, xylene or benzene, preferably toluene, at a temperature from about room temperature to about 100° C., preferably about 100° C. A palladium catalyst such as tetrakis(triphenylphosphine)palladium(0) (Pd(PPh$_3$)$_4$), BnPdCl(PPh$_3$)$_2$, or PdCl$_2$(PPh$_3$)$_2$, preferably Pd(PPh$_3$)$_4$, may be used.

Tert-butyl-dimethyl-(2-vinyl-5-methoxy-benzyloxy)-silane (15) is reduced to tert-butyl-dimethyl-(2-ethyl-5-methoxy-benzyloxy)-silane (16) using a hydrogenation catalyst, preferably platinum oxide, under a hydrogen pressure of about 1 to 4 atmospheres, preferably under a hydrogen pressure of about 2 atmospheres. Suitable solvents include methanol, ethanol, ethyl acetate and acetic acid, preferably ethyl acetate. Catalysts such as 10% palladium (Pd) on calcium carbonate, Rh—C or Pd—C may also be used. The reaction is generally carried out at about room temperature.

In a bromination reaction, tert-butyl-dimethyl-(2-ethyl-5-methoxy-benzyloxy)-silane (16) is converted to tert-butyl-dimethyl-(4-bromo-2-ethyl-5-methoxy-benzyloxy)-silane (17) using N-bromosuccinimide (NBS) followed by the addition of silica gel 60 (EM Science, 480 Democrat Road, Gibbstown, N.J. 08027, an affiliate of Merck KGaA, Darmstadt, Germany). The reaction is allowed to stir in the absence of light. The reaction may also be carried out using NBS without silica gel, or using bromine instead of NBS. Suitable solvents include carbon tetrachloride, chloroform, acetic acid and carbon disulfide, preferably carbon tetrachloride. The reaction may be carried out at about room temperature.

Tert-butyl-dimethyl-(4-bromo-2-ethyl-5-methoxy-benzyloxy)-silane (17) is cooled to about −78° C. in tetrahydrofuran (THF) and treated with n-butyl lithium. The reaction mixture is then treated with triethyl borate, at about −78° C., and allowed to warm to room temperature. Following acid workup, the reaction mixture yields tert-butyl-dimethyl-(4-boronic acid-2-ethyl-5-methoxy-benzyloxy)-silane (18). THF is the preferred solvent, but other suitable solvents such as diethyl ether may also be used. Similarly, n-butyl lithium is the preferred reagent, but other suitable reagents such as t-butyl lithium may also be used.

In a Suzuki coupling reaction, 2-bromo-6-(N-2,2-dimethylpropamido)pyridine and tert-butyl-dimethyl-(4-boronic acid-2-ethyl-5-methoxy-benzyloxy)-silane (18) are treated with sodium carbonate and tetrakis(triphenylphosphine)palladium(0) (Pd(PPh$_3$)$_4$) in ethanol and water. The reaction is heated to reflux to yield 2-2-(4-tert-butyldimethylsilyloxymethyl-5-ethyl-2-methoxy-phenyl)-6-(N-2,2-dimethylpropamido)-pyridine (19). Tetrakis(triphenylphosphine)palladium(0) is the preferred catalyst. However, other suitable palladium catalysts include Pd(OAc)$_2$, Pd$_2$(dba)$_3$ and [(allyl)PdCl]$_2$. Similarly, ethanol/water is the preferred solvent, but other suitable solvents such as tetrahydrofuran (THF), acetone, benzene and dimethoxyethane (DME) may be used.

The tert-butyl-dimethylsilyl protecting group is removed from the 2-2-(4-tert-butyldimethylsilyloxymethyl-5-ethyl-2-methoxy-phenyl)-6-(N-2,2-dimethylpropamido)-pyridine (19) by treatment with 1M tetrabutylammonium fluoride (TBAF) in tetrahydrofuran (THF) at about room temperature. The reaction yields 2-(4-hydroxymethyl-5-ethyl-2-methoxy-phenyl)-6-(N-2,2-dimethylpropamido)-pyridine (20). Although TBAF is the preferred reagent, other reagents such as KF/18-crown-6 and TBACl/KF may also be used. Similarly, although THF is the preferred solvent, other solvents such as diethyl ether and acetonitrile may be used.

The alcohol, 2-(4-hydroxymethyl-5-ethyl-2-methoxy-phenyl)-6-(N-2,2-dimethylpropamido)-pyridine (20), is oxidized to the corresponding aldehyde, 2-(4-formyl-5-ethyl-2-methoxy-phenyl)-6-(N-2,2-dimethylpropamido)-pyridine (21), by treatment with manganese dioxide in toluene. In addition to the preferred catalyst, manganese dioxide, other suitable catalysts include BaMnO$_4$ and AgMnO$_4$. Benzene may also be used as the solvent in the above reaction, although toluene is preferred. The above reaction is carried out at a temperature from about room temperature to about 100° C., preferably about 90° C.

Reductive amination of the aldehyde, 2-(4-formyl-5-ethyl-2-methoxy-phenyl)-6-(N-2,2-dimethylpropamido)-pyridine (21), with N,N-dimethylamine yields the amine, 2-(4-N,N-dimethylaminomethyl-5-ethyl-2-methoxy-phenyl)-6-(N-2,2-dimethylpropamido)-pyridine (22). This reductive amination is accomplished by treating 2-(4-formyl-5-ethyl-2-methoxy-phenyl)-6-(N-2,2-dimethylpropamido)-pyridine (21) in dichloromethane with N,N-dimethylamine in tetrahydrofuran (THF), sodium triacetoxyborohydride and acetic acid at about room temperature. Other suitable reducing agents include sodium cyanoborohydride.

The aminopyridine protecting group is removed from the 2-(4-N,N-dimethylaminomethyl-5-ethyl-2-methoxy-phenyl)-6-(N-2,2-dimethylpropamido)-pyridine (22) by treatment with 6N hydrogen chloride in dioxane at a temperature from about room temperature to about the reflux temperature, preferably at about the reflux temperature. The reaction yields the compound of formula II, 6-[4-(N,N-dimethylaminomethyl)-5-ethyl-2-methoxy-phenyl]-pyridin-2-ylamine (23). Aside from the 6N hydrogen chloride, which is preferred, other reagents that may be used in the above reaction include sodium hydroxide/methanol and barium hydroxide/methanol. Aside from dioxane, which is also preferred, other solvents that may be used include methanol/water and ethanol/water.

Alternatively, reductive amination of the aldehyde, 2-(4-formyl-5-ethyl-2-methoxy-phenyl)-6-(N-2,2-dimethylpropamido)-pyridine (21), with N-methylamine yields the amine, 2-(4-N-methylaminomethyl-5-ethyl-2-methoxy-phenyl)-6-(N-2,2-dimethylpropamido)-pyridine (24). This reductive amination is accomplished by combining 2-(4-formyl-5-ethyl-2-methoxy-phenyl)-6-(N-2,2-dimethylpropamido)-pyridine (21) in dichloromethane with N-methylamine in tetrahydrofuran (THF), acetic acid and sodium triacetoxyborohydride. The reaction is carried out at a temperature from about 0° C. to about room temperature, preferably about room temperature. Other suitable reducing agents include sodium cyanoborohydride.

The aminopyridine protecting group is removed from the 2-(4-N-methylaminomethyl-5-ethyl-2-methoxy-phenyl)-6-(N-2,2-dimethylpropamido)-pyridine (24) by treatment with dioxane and 6N hydrogen chloride at a temperature of about room temperature to about the reflux temperature, preferably at about the reflux temperature. The reaction yields the compound of formula III, 6-[4-(N-methylaminomethyl)-5-ethyl-2-methoxy-phenyl]-pyridin-2-ylamine (25). Aside from the 6N hydrogen chloride, which is preferred, other reagents which may be used in the above reaction include sodium hydroxide/methanol and barium hydroxide/methanol. Aside from dioxane, which is also preferred, other solvents which may be used include methanol/water and ethanol/water.

The starting materials used in the procedures of Scheme 2, the syntheses of which are not described above, are either commercially available, known in the art or readily obtainable from known compounds using methods that will be apparent to those skilled in the art.

The compounds of formulas II and III, and the intermediates shown in the above reaction schemes can be isolated and purified by conventional procedures, such as recrystallization or chromatographic separation.

In each of the reactions discussed or illustrated above, pressure is not critical unless otherwise indicated. Pressures from about 0.5 atmospheres to about 5 atmospheres are generally acceptable, and ambient pressure, i.e., about 1 atmosphere, is preferred as a matter of convenience.

This invention relates to the compounds of formulas I, II, III and IV, and their pharmaceutically acceptable salts. The compounds of formulas I, II, III, and IV, and their pharmaceutically acceptable salts, are hereinafter collectively referred to as "the active compounds of the present invention." The active compounds of the present invention can be administered to mammals via either the oral, parenteral (such as subcutaneous, intravenous, intramuscular, intrasternal and infusion techniques), rectal, intranasal or topical routes. In general, these compounds are most desirably administered in doses ranging from about 0.01 mg to about 1500 mg per day, in single or divided doses (i.e., from 1 to 4 doses per day), although variations will necessarily occur depending upon the species, weight and condition of the subject being treated and the particular route of administration chosen. However, a dosage level that is in the range of about 0.5 mg to about 500 mg per kg of body weight per day is most desirably employed. Nevertheless, variations may occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such higher dosage levels are first divided into several small doses for administration throughout the day.

The active compounds of the present invention may be administered alone or in combination with pharmaceutically acceptable carriers or diluents by either of the routes previously indicated, and such administration may be carried out in single or multiple doses. More particularly, the active compounds of the present invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), alginic acid and certain complex silicates, together with granulation binders such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules. Preferred materials in this connection include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions containing an active compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well known to those skilled in the art.

Additionally, it is also possible to administer the active compounds of the present invention topically when treating inflammatory conditions of the skin. This may be done by way of creams, jellies, gels, pastes, patches, ointments and the like, in accordance with standard pharmaceutical practice.

The active compounds of the present invention are useful as NOS inhibitors i.e., they possess the ability to inhibit the NOS enzyme in mammals, and therefore they are able to function as therapeutic agents in the treatment of the aforementioned disorders and diseases in an afflicted mammal.

The ability of compounds of the formulas I, II, III and IV of this invention, and their pharmaceutically acceptable salts, to inhibit NOS may be determined using procedures described in the literature. The ability of compounds of the present invention to inhibit endothelial NOS may be determined by using the procedures described by Schmidt et al. in *Proc. Natl. Acad. Sci. U.S.A.*, 88, pp. 365–369 (1991) and by Pollock et al., in *Proc. Natl. Acad. Sci. U.S.A.*, 88, pp. 10480–10484 (1991). The ability of compounds of the present invention to inhibit inducible NOS may be determined using the procedures described by Schmidt et al., in *Proc. Natl. Acad, Sci. U.S.A.*, 88 pp. 365–369 (1991) and by Garvey et al. in *J. Biol. Chem.*, 269, pp. 26669–26676 (1994). The ability of the compounds of the present invention to inhibit neuronal NOS may be determined using the procedure described by Bredt and Snyder in *Proc. Natl. Acad. Sci. U.S.A.*, 87, 682–685 (1990).

As indicated above, inhibition of NO synthase activity may be determined by conversion of [$^3$H]arginine to [$^3$H] citrulline as described by Bredt and Snyder in *Proc. Natl. Acad. Sci. U.S.A.*, 87, 682–685 (1990), but with slight modification. Specifically, 10 uL of crude enzyme lysate and 10 uL of 350 nM [$^3$H]arginine are added to 100 uL of buffer containing 10 mM Hepes, 0.32 M sucrose, 0.75 mM NADPH, 0.1 mM EDTA, 0.63 mM $CaCl_2$, 1 mM dithiothreitol, 30 nM calmodulin(CaM), 2 uM Flavin Adenin dinucleotie (FAD), 2 uM Flavin mononucleotide (FMN), 3 uM tetrahydrobiopterin ($H_4B$) and trace bovine serum albumin in 96-well plate format. After incubation for 50 minutes at 30° C., assays are terminated by application to 75 uL BioRex-70 resin (H⁺ form) and eluted with 90 uL of water. [³H]citrulline may be quantified by liquid scintillation spectroscopy of the total flow-through.

The title compounds of Examples 1–4 below were tested according to the foregoing procedure and each exhibited an $IC_{50}<1$ μM for inhibition of neuronal NOS.

The present invention is illustrated by the following examples. It will be understood, however, that the invention is not limited to the specific details of these examples. Melting points are uncorrected. Proton nuclear magnetic resonance spectra ($^1$H NMR) and $^{13}$C nuclear magnetic resonance spectra were measured for solutions in deuterochloroform ($CDCl_3$) or in $CD_3OD$ or $CD_3SOCD_3$ and peak positions are expressed in parts per million (ppm) downfield from tetramethylsilane (TMS). The peak shapes are denoted as follows: s, singlet; d, doublet; t, triplet; q, quartet, m, multiplet, b, broad.

Preparation 1

2-ethyl-5-methoxyphenol (2)

Under a nitrogen atmosphere, 36.70 g (120.4 mmol) of 2-acetyl-5-methoxyphenol (1) was combined with 20.13 ml (144.4 mmol) of triethylamine in 150 mL of anhydrous THF. The reaction mixture was cooled to 0° C., and 13.81 ml (144.4 mmol) of ethyl chloroformate was added dropwise to the reaction mixture over a 30 minute period. The reaction mixture was allowed to stir for an additional 30 minutes. The resultant white solids were filtered. A solution of 13.64 g (361.1 mmol) of sodium borohydride in 200 ml of water was added dropwise to the filtrate over a period of 45 minutes at a temperature of 5–10° C. The reaction mixture was allowed to warm to room temperature and stirred for 1.5 hours. The resultant solution was acidified to pH 2 with 1M HCl and extracted with ether (1×250 ml). The ether layer was then extracted with 10% sodium hydroxide (5×100 mL). The combined base extracts were acidified with concentrated HCl and extracted with ether. The combined ether extracts were washed with water (1×100 ml), dil $NaHCO_3$ (1×100 ml) and brine (1×100 mL), dried over sodium sulfate, filtered and concentrated in vacuo to yield 18.37 g of crude product, 2-ethyl-5-methoxyphenol (2), as a colorless oil. The crude product was used in Preparation 2 below.

$^1$H NMR ($CDCl_3$): 1.20 (t-3H; J=7.26 Hz), 1.87 (bs-1H), 2.55 (q-2H), 3.75 (s-3H), 6.35 (d-1H, J=0.5 Hz), 6.44 (dd-1H), 7.01 (d-1H, J=8.3 Hz).

Preparation 2

3-benzyloxy-4-ethyl-1-methoxybenzene (3)

Under a nitrogen atmosphere, 18.30 g (120.2 mmol) of 2-ethyl-5-methoxyphenol (2) was dissolved in 150 ml of acetone. To this solution was added 33.24 g (240.5 mmol) of potassium carbonate followed by 15.02 ml (126.3 mmol) of benzyl bromide. The resultant mixture was heated to reflux for 16 hours. The reaction mixture was concentrated in vacuo and partitioned between ethyl acetate (300 ml) and water (300 ml). The ethyl acetate layer was separated, washed with 1M NaOH (2×200 mL) and brine (1×200 mL), dried over sodium sulfate, filtered and concentrated in vacuo to yield 29.70 g of crude 3-benzyloxy-4-ethyl-1-methoxybenzene (3). Chromatography of the crude product on 400 g of silica gel 60 (EM Science) using 97:3 hexane: ethyl acetate yielded 12.62 g (43%) of 3-benzyloxy-4-ethyl-1-methoxybenzene (3).

$^1$H NMR ($CDCl_3$): 1.20 (t-3H; J=7.47 Hz), 2.64 (q-2H; J=7.47 Hz), 3.78 (s-3H), 5.06 (s-2H), 6.45 (dd-1H, J=2.29, 8.30 Hz), 6.50 (d-1H; J=2.28 Hz), 7.07 (d-1H, J=8.30 Hz), 7.30–7.45 (m-5H).

Preparation 3

5-benzyloxy-2-bromo-4-ethyl-1-methoxybenzene (4)

Under a nitrogen atmosphere, 12.60 g (52.00 mmol) of 3-benzyloxy-4-ethyl-1-methoxybenzene (3) and 9.72 g (54.60 mmol) of NBS were combined in 350 mL of carbon tetrachloride, followed by the addition of 50 g of silica gel 60 (EM Science). The reaction was allowed to stir for 16 hours in the absence of light. The reaction mixture was filtered and the silica gel was washed with dichloromethane. The filtrate was washed with ethyl acetate (1×300 mL). The combined organic extracts were washed with 1M NaOH (2×300 mL), dilute $NaHSO_3$ (1×200 mL) and brine (1×200 mL), dried over magnesium sulfate, filtered and concentrated in vacuo to yield 16.82 g (100%) of crude, 5-benzyloxy-2-bromo-4-ethyl-1-methoxybenzene (4) as a colorless oil.

$^1$H NMR ($CDCl_3$): 1.17 (t-3H; J=7.48 Hz), 2.60 (q-2H; J=7.48 Hz), 3.82 (s, 3H), 5.07 (s-2H), 6.50 (s, 1H), 7.25–7.44 (m-6H).

Preparation 4

4-benzyloxy-5-ethyl-2-methoxy-phenylboronic acid (5)

Under a nitrogen atmosphere, 16.70 g (52.00 mmol) of 5-benzyloxy-2-bromo-4-ethyl-1-methoxybenzene (4) was added to 110 mL of anhydrous THF. The solution was cooled to −78° C., and 22.88 mL (57.19 mmol) of a 2.5 M solution of butyl lithium was added dropwise while maintaining the temperature below −70° C. The reaction mixture was stirred at −78° C. for 45 minutes. 9.73 mL (57.19 mmol) of triethyl borate was then added, and the reaction was allowed to stir at −78° C. for an additional 2 hours. The reaction mixture was then allowed to warm to 23° C. over a 30 minute period and was quenched with 100 mL of saturated $NH_4Cl$. The pH was adjusted to 5.0 with 1M HCl, and the resultant solution was extracted with ethyl acetate (2×200 mL). The combined extracts were washed with brine (1×100 mL), dried over sodium sulfate, filtered and concentrated in vacuo to yield crude product as a greenish-tan solid. The crude product was triturated with hexane and filtered to afford 10.65 g (64%) of 4-benzyloxy-5-ethyl-2-methoxy-phenylboronic acid (5) as an off-white solid.

$^1$H NMR ($CDCl_3$): 1.19 (t-3H), 2.62 (q-2H), 3.85 (s, 3H), 5.13 (s-2H), 5.77 (bs, 2H), 6.47 (s, 1H), 7.25–7.59 (m-6H).

Preparation 5

2-(4-benzyloxy-5-ethyl-2-methoxy-phenyl)-6-(2,5-dimethyl-pyrrol-1-yl)-pyridine (6)

Under a nitrogen atmosphere, 5.00 g (19.91 mmol) of 2-bromo-6-(2,5-dimethylpyrrol-1-yl)pyridine, 5.98 g (20.91 mmol) of 4-benzyloxy-5-ethyl-2-methoxy-phenylboronic acid (5), 8.44 g (79.64 mmol) of sodium carbonate and 1.15 g (0.996 mmol) of tetrakis(triphenylphosphine)palladium(0) were combined in 90 mL of ethanol and 10 mL of water. The solution was allowed to reflux for 64 hours, and then the reaction mixture was concentrated in vacuo. The resultant yellow residue was partitioned between ethyl acetate (200 mL) and water (200 mL). The aqueous layer was extracted again with ethyl acetate (200 mL). The combined organic extracts were washed with brine (1×200 mL), dried over sodium sulfate, filtered and concentrated in vacuo to yield crude product as a yellow oil which crystallized upon standing. Recrystallization of this solid from absolute ethanol afforded 6.00 g (73%) of 2-(4-benzyloxy-5-ethyl-2-methoxy-phenyl)-6-(2,5-dimethyl-pyrrol-1-yl)-pyridine (6) as a tan solid.

$^1$H NMR (CDCl$_3$): 1.21 (t-3H; J=7.47 Hz), 2.22 (s-6H), 2.67 (q-2H; J=7.47 Hz), 3.85 (s, 3H), 5.15 (s-2H), 5.91 (s-2H), 6.56 (s, 1H), 7.04–7.91 (m-9H).

Preparation 6

4-[6-(2,5-Dimethyl-pyrrol-1-yl)-pyridin-2-yl]-6-ethyl-3-methoxyphenol (7)

Under a nitrogen atmosphere, 5.90 g (14.30 mmol) of 2-(4-benzyloxy-5-ethyl-2-methoxy-phenyl)-6-(2,5-dimethyl-pyrrol-1-yl)-pyridine (6) and 27.06 g (429.1 mmol) of ammonium formate were combined in 125 mL of methanol and 500 mg of 20% Pd(OH)$_2$ on carbon. The resultant slurry was allowed to reflux for 45 minutes. 500 mg of 20% Pd(OH)$_2$ on carbon was added twice more, and the resultant slurry was allowed to reflux for 45 minutes. The reaction mixture was then allowed to cool to ambient temperature and passed through a pad of celite to remove the catalyst. The filtrate was concentrated in vacuo and the resultant yellow residue was partitioned between ethyl acetate (200 mL) and water (200 mL). The aqueous layer was extracted again with ethyl acetate (200 mL). The combined organic extracts were washed with brine (1×200 mL), dried over sodium sulfate, filtered and concentrated in vacuo to yield 4.52 g (98%) of 4-[6-(2,5-Dimethyl-pyrrol-1-yl)-pyridin-2-yl]-6-ethyl-3-methoxyphenol (7) as a tan solid.

$^1$H NMR (CDCl$_3$): 1.20 (t-3H; J=7.41 Hz), 2.20 (s-6H), 2.55 (q-2H; J=7.41 Hz), 3.82 (s, 3H), 5.45 (bs-1H), 5.90 (s-2H), 6.50 (s, 1H), 7.04 (dd-1H; J=0.99, 7.74 Hz), 7.70 (s-1H), 7.76–7.91 (m-2H).

Preparation 7

4-(6-Amino-pyridin-2-yl)-2-ethyl-5-methoxyphenol (8)

Under a nitrogen atmosphere, 4.50 g (13.96 mmol) of 4-[6-(2,5-Dimethyl-pyrrol-1-yl)-pyridin-2-yl]-6-ethyl-3-methoxyphenol (7) and 11.64 g (167.5 mmol) of hydroxylamine hydrochloride were combined in 84 mL of ethanol and 14 mL of water. The resultant mixture was allowed to reflux for 16 hours. The reaction mixture was then allowed to cool to ambient temperature and concentrated in vacuo. The resultant yellow residue was partitioned between ethyl acetate (200 mL) and dilute sodium bicarbonate (200 mL). The aqueous layer was extracted again with ethyl acetate (2×200 mL). The combined organic extracts were washed with brine (1×200 mL), dried over sodium sulfate, filtered and concentrated in vacuo to yield crude product as a brown solid. Chromatography of the crude product on 250 g of silica gel 60 (EM Science) using 4:1 ethyl acetate: hexane yielded 1.86 g (55%) of 4-(6-Amino-pyridin-2-yl)-2-ethyl-5-methoxyphenol (8) as a salmon colored solid.

$^1$H NMR (CD$_3$OD): 1.21 (t-3H; J=7.41 Hz), 1.87 (s-2H), 2.40 (s-1H), 2.61 (q-2H; J=7.41 Hz), 3.78 (s-3H), 6.46 (dd-1H, J=0.82, 8.14 Hz), 6.52 (s-1H), 6.92 (dd-1H, J=0.82, 7.41), 7.26 (s-1H), 7.45 (dd-1H).

Preparation 8

6-[4-(3-azetidinoxy-1-carboxylic acid tert-butyl ester)-5-ethyl-2-methoxy-phenyl]-pyridin-2-ylamine (10)

Under a nitrogen atmosphere, 100 mg (0.41 mmol) of 4-(6-Amino-pyridin-2-yl)-2-ethyl-5-methoxyphenol (8) and 92 mg (0.82 mmol) of potassium t-butoxide were combined in 8 mL of anhydrous DMSO. The reaction mixture was allowed to stir for 10 minutes. 206 mg (0.82 mmol) of 3-methanesulfonyloxy-azetidine-1-carboxylic acid tert-butyl ester in 2 mL of anhydrous DMSO was added to the reaction mixture, followed by the addition of 50 mg of tetrabutylammonium iodide. The reaction mixture was heated to 100° C. and stirred for 18.5 hours. The reaction mixture was then allowed to cool to room temperature. Ethyl acetate (100 mL) was added, and the solution was washed with 1N NaOH (1×100 mL) and brine (1 ×100 mL), dried over sodium sulfate, filtered and concentrated in vacuo to yield crude product. The crude product was chromatographed on a Flash 12M silica gel column with 100% ethyl acetate. The crude product was then concentrated in vacuo and rechromatographed with 0 to 3% methanol in dichloromethane to afford 142 mg (87%) of 6-[4-(3-azetidinoxy-1-carboxylic acid tert-butyl ester)-5-ethyl-2-methoxy-phenyl]-pyridin-2-ylamine (10) as an off-white solid.

$^1$H NMR (CDCl$_3$): 1.18 (t-3H; J=7.3 Hz), 1.44 (s-9H), 2.60 (s-2H), 2.61 (q-2H), 3.76 (s-3H), 4.00–4.44 (m-4H), 4.92 (m-1H), 6.10(s-1H), 6.39 (m-1H), 7.10 (m-1H), 7.42 (m-1H), 7.53 (s-1H).

EXAMPLE 1

6-[4-(N-methyl-3-azetidinoxy)-5-ethyl-2-methoxy-phenyl]-pyridin-2-ylamine (12)

Under a nitrogen atmosphere, 357 mg (0.92 mmol) of crude 6-[4-(3-azetidinoxy-1-carboxylic acid tert-butyl ester)-5-ethyl-2-methoxy-phenyl]-pyridin-2-ylamine (10) and 39 mg (1.02 mmol) of lithium aluminum hydride were added to 15 mL of anhydrous THF. The reaction mixture was heated to reflux for 16 hours, and then an additional 75 mg (2.04 mmol) of lithium aluminum hydride was added. After 2 hours, the reaction mixture was allowed to cool to ambient temperature. The reaction mixture was then carefully quenched sequentially with 114 ul of water, 114 ul of 1N NaOH and 342 ul of water. The aluminum salts were filtered and washed with ethyl acetate, and the filtrate was dried over sodium sulfate and concentrated in vacuo to yield crude product. The crude product was chromatographed on a Flash 12M silica gel column with 5 to 10% methanol in dichloromethane to afford 48 mg (38%) of 6-[4-(N-methyl-3-azetidinoxy)-5-ethyl-2-methoxy-phenyl]-pyridin-2-ylamine (12). The 6-[4-(N-methyl-3-azetidinoxy)-5-ethyl-2-methoxy-phenyl]-pyridin-2-ylamine (12) was converted to its dihydrochloride salt by dissolving the aminopyridine (12) in dichloromethane and adding 1 ml of an ether solution saturated with HCl. The resultant residue was concentrated and triturated with ethylacetate.

$^1$H NMR (CDCl$_3$): 1.17 (t-3H; J=7.58 Hz), 2.40 (s-3H), 2.59 (m-2H), 3.07–3.11 (m-2H), 3.75 (s-3H), 3.83–3.89 (m-2H), 4.39 (bs-2H), 4.77 (m-1H), 6.20 (s-1H), 6.37 (d-1H; J=8.07 Hz), 7.09 (m-1H), 7.41 (m-1H), 7.51 (s-1H).

EXAMPLE 2

6-[4-(3-azetidinoxy)-5-ethyl-2-methoxy-phenyl]-pyridin-2-ylamine (11)

Under a nitrogen atmosphere, 82 mg (0.21 mmol) of 6-[4-(3-azetidinoxy-1-carboxylic acid tert-butyl ester)-5-ethyl-2-methoxy-phenyl]-pyridin-2-ylamine (10) and 10 mL of TFA were added to 20 mL of dichloromethane. The reaction mixture was allowed to stir for 1.5 hours at ambient temperature, and then concentrated in vacuo to yield crude amine. This crude product was partitioned between saturated NaHCO$_3$ (25 mL) and dichloromethane (100 mL). The organic layer was dried over sodium sulfate, filtered and concentrated in vacuo. This material was chromatographed on a Flash 12M silica gel column, beginning with 1% and increasing to 10% methanol in dichloromethane, to afford 26 mg (43%) of 6-[4-(3-azetidinoxy)-5-ethyl-2-methoxy-phenyl]-pyridin-2-ylamine (11).

$^1$H NMR (CDCl$_3$): 1.17 (t-3H), 2.59 (m-2H), 3.20 (bs-1H), 3.76 (s-3H), 3.80–4.00 (m-4H), 4.50 (bs-2H), 5.00 (m-1H), 6.14 (s-1H), 6.37 (m-1H), 7.07 (m-1H), 7.42 (m-1H), 7.50 (s-1H).

Preparation 9

2-bromo-5-methoxybenzyl alcohol (13)

Under a nitrogen atmosphere, 25 g (0.11 mol) of 2-bromo-5-methoxybenzoic acid was dissolved in 100 mL of anhydrous THF. 140 mL (0.14 mol) of borane (1 M in THF) was added to this solution over a period of 1 hour. The reaction was allowed to stir and was carefully quenched with 1:1 THF: saturated K$_2$CO$_3$. Ether was added and the aqueous and organic layers were separated. The aqueous layer was extrated again with ether (2×100 mL). The combined organic extracts were dried over sodium sulfate, filtered and concentrated in vacuo to afford 23.0 g (96%) of 2-bromo-5-methoxybenzyl alcohol (13).

$^1$H NMR (CDCl$_3$): 2.02 (t-1H; J=6.23 Hz), 3.79 (s-3H), 4.69 (d-2H; J=6.23 Hz), 6.70 (dd-1H; J=3.12, 8.72 Hz), 7.04 (d-1H; J=3.12 Hz), 7.39 (d-1H; J=8.72 Hz).

Preparation 10

(2-bromo-5-methoxy-benzyloxy)-tert-butyl-dimethyl-silane (14)

Under a nitrogen atmosphere, 23.0 g (0.11 mol) of 2-bromo-5-methoxybenzyl alcohol (13) was dissolved in 100 mL of anhydrous THF. 14.43 g (0.21 mol) of imidazole was added, followed by 17.6 g (0.12 mol) of t-butyl dimethylsilylchloride. The reaction mixture was allowed to stir overnight at ambient temperature. Ether was added and the reaction was diluted with water (200 mL). The aqueous layer was separated and extracted with ether (2×300 mL). The combined organic extracts were dried over sodium sulfate, filtered and concentrated in vacuo to afford crude product. The crude product was loaded onto a 4 inch×6 inch silica gel column. Using 40% ether in hexane as an eluant afforded 33.63 g (96%) of (2-bromo-5-methoxy-benzyloxy)-tert-butyl-dimethyl-silane (14).

$^1$H NMR (CDCl$_3$): 0.12 (s-3H), 0.12 (s-3H), 0.96 (s-9H), 3.78 (s-3H), 4.67 (s-2H), 6.64 (m-1H), 7.14 (d-1H; J=3.11 Hz), 7.34 (d-1H; J=8.71 Hz).

Preparation 11 tert-butyl-dimethyl-(2-vinyl-5-methoxy-benzyloxy)-silane (15)

Under a nitrogen atmosphere, 33.63 9 (0.10 mol) of (2-bromo-5-methoxy-benzyloxy)-tert-butyl-dimethyl-silane (14), 32.18 9 (0.10 mol) of tributylvinyl tin and 4.7 g (0.004 mol) of tetrakis(triphenylphosphine)palladium(0) were combined in 250 mL of toluene, and the solution was heated to reflux for 6 hours. The reaction was allowed to cool to ambient temperature and was quenched with 5% NH$_4$OH (2×100 mL). The organic layer was washed with water (1×200 mL) and brine (1×200 mL), dried over sodium sulfate, filtered and concentrated in vacuo to yield crude product. The crude product was chromatographed on a silica gel column, first with hexane, then with 20% CHCl$_3$ in hexane, and finally with 40% CHCl$_3$ in hexane to afford 25.0 9 (89%) of tert-butyl-dimethyl-(2-vinyl-5-methoxy-benzyloxy)-silane (15).

$^1$H NMR (CDCl$_3$): 0.10 (s-6H), 0.95 (s-9H), 3.81 (s-3H), 4.77 (s-2H), 5.18 (dd-1H); J=11.0, 1.45 Hz), 5.52 (dd-1H; J=17.45, 1.45 Hz), 6.77 (m-2H), 7.05 (d-1H; J=2.70 Hz), 7.40 (d-1H; J=8.51 Hz).

Preparation 12 tert-butyl-dimethyl-(2-ethyl-5-methoxy-benzyloxy)-silane (16)

25.0 g (0.0899 mol) of tert-butyl-dimethyl-(2-vinyl-5-methoxy-benzyloxy)-silane (15) was dissolved in 100 mL of ethyl acetate and was placed in a 1 L Parr Shaker bottle. 1.93 g (0.0084 mol) of catalyst (PtO$_2$) was added and the solution was placed under 30 PSI of hydrogen for 25 minutes. The reaction mixture was filtered through a pad of celite and concentrated in vacuo to yield crude product. The crude product was chromatographed on a silica gel column with 40% CHCl$_3$ in hexane to afford 24.85 g (99%) of tert-butyl-dimethyl-(2-ethyl-5-methoxy-benzyloxy)-silane (16).

$^1$H NMR (CDCl$_3$): 0.11 (s-6H), 0.95 (s-9H), 1.18 (t-3H; J=7.68 Hz), 2.52 (m-2H), 3.79 (s-3H), 4.72 (s-2H), 6.75 (m-1H), 7.06 (m-2H).

Preparation 13 tert-butyl-dimethyl-(4-bromo-2-ethyl-5-methoxy-benzyloxy)-silane (17)

Under a nitrogen atmosphere, 24.85 9 (0.0885 mol) of tert-butyl-dimethyl-(2-ethyl-5-methoxy-benzyloxy)-silane (16) and 15.77 g (0.0885 mmol) of NBS were combined in 500 mL of carbon tetrachloride, followed by the addition of 100 g of silica gel 60 (EM Science). The reaction was allowed to stir for 16 hours in the absence of light. The reaction mixture was filtered and the silica gel was washed with dichloromethane. The filtrate was washed with dichloromethane (1×300 mL). The combined organic extracts were washed with 1M NaOH (2×300 mL), dilute NaHSO$_3$ (1×200 mL) and brine (1×200 mL), dried over magnesium sulfate, filtered and concentrated in vacuo to yield crude tert-butyl-dimethyl-(4-bromo-2-ethyl-5-methoxy-benzyloxy)-silane (17). Crude tert-butyl-dimethyl-(4-bromo-2-ethyl-5-methoxy-benzyloxy)-silane (17) was chromatographed on a silica gel column with 20% CHCl$_3$ in hexane to afford 19.70 g (62%) of tert-butyl-dimethyl-(4-bromo-2-ethyl-5-methoxy-benzyloxy)-silane (17).

$^1$H NMR (CDCl$_3$): 0.10 (s-6H), 0.94 (s-9H), 1.16 (t-3H; J=7.68 Hz), 2.47 (m-2H), 3.87 (s-3H), 4.67 (s-2H), 7.09 (s-1H), 7.29 (s-1H).

Preparation 14 tert-butyl-dimethyl-(4-boronic acid-2-ethyl-5-methoxy-benzyloxy)-silane (18)

Under a nitrogen atmosphere, 10.00 g (0.027 mol) of tert-butyl-dimethyl-(4-bromo-2-ethyl-5-methoxy-benzyloxy)-silane (17) was added to 250 mL of anhydrous THF. The solution was cooled to −78° C., and 12.25 mL (0.031 mol) of a 2.5 M solution of butyl lithium was added dropwise while maintaining the temperature below −70° C. The reaction mixture was stirred at −78° C. for 1 hour, and then the temperature was raised to −30° C. 5.21 mL (0.031 mol) of triethyl borate was added to the reaction mixture. The reaction was allowed to warm to 23° C. over a 2 hour period and was quenched with 100 mL of saturated NH$_4$Cl. The pH was adjusted to 5.0 with 1M HCl, and the resultant solution was extracted with ethyl acetate (2×200 mL). The combined extracts were washed with brine (1×100 mL), dried over sodium sulfate, filtered and concentrated in vacuo to afford 9.0 g (100%) of crude tert-butyl-dimethyl-(4-boronic acid-2-ethyl-5-methoxy-benzyloxy)-silane (18) which was used directly in Preparation 14.

$^1$H NMR (CDCl$_3$): 0.12 (s-6H), 0.96 (s-9H), 1.18 (t-3H), 2.51(m-2H), 3.90 (s-3H), 4.76 (s-2H), 7.12 (s-1H), 7.25 (s-1H), 7.57 (s-1H).

Preparation 15

2-(4-tert-butyldimethylsilyoxymethyl-5-ethyl-2-methoxy-phenyl)-6-(N-2,2-dimethylpropamido)-pyridine (19)

Under a nitrogen atmosphere, 6.49 g (0.025 mol) of 2-bromo-6-(N-2,2-dimethylpropamido)pyridine, 9.0 g (0.027 mol) of tert-butyl-dimethyl-(4-boronic acid-2-ethyl-5-methoxy-benzyloxy)-silane (18), 10.6 g (0.10 mol) of sodium carbonate and 5.85 g (0.005 mol) of tetrakis (triphenylphosphine)palladium(0) were combined in 180 mL of ethanol and 20 mL of water. The solution was allowed to reflux for 18 hours. The reaction mixture was then concentrated in vacuo. The resultant yellow residue was partitioned between ethyl acetate (200 mL) and water (200 mL). The aqueous layer was extracted again with ethyl acetate (200 mL). The combined organic extracts were washed with brine (1×200 mL), dried over sodium sulfate, filtered and concentrated in vacuo to yield crude 2-(4-tert-butyldimethylsilyloxymethyl-5-ethyl-2-methoxy-phenyl)-6-(N-2,2-dimethylpropamido)-pyridine (19). The crude 2-(4-tert-butyidimethylsilyloxymethyl-5-ethyl-2-methoxy-phenyl)-6-(N-2,2-dimethylpropamido)-pyridine (19) was chromatographed on a silica gel column with 20% ether in hexane to afford 13.93 g of still crude 2-(4-tert-butyl dimethylsilyloxymethyl-5-ethyl-2-methoxy-phenyl)-6-(N-2,2-dimethylpropamido)-pyridine (19) which was used directly in Preparation 15.

$^1$H NMR (CDCl$_3$): 0.13 (s-6H), 0.96 (s-9H), 1.21 (t-3H; J=7.48 Hz), 1.32 (s-9H), 2.57(m-2H), 3.83 (s-3H), 4.78 (s-2H), 7.19 (s-1H), 7.46 (s-1H), 7.52 (m-1H), 7.68 (t-1H), 8.07 (bs-1H), 8.12 (dd-1H; J=0.83, 8.10 Hz).

Preparation 16

2-(4-hydroxymethyl-5-ethyl-2-methoxy-1phenyl)-6-(N-2,2-dimethylpropamido)-pyridine (20)

Under a nitrogen atmosphere, 76.34 mL (0.76 mol) of 1M TBAF in THF was added to a THF (100 mL) solution containing 13.93 g of crude 2-(4-tert-butyldimethylsilyloxymethyl-5-ethyl-2-methoxy-phenyl)-6-(N-2,2-dimethylpropamido)-pyridine (19). The solution was allowed to stir for 18 hours. The reaction mixture was then concentrated in vacuo. The resultant residue was partitioned between ether (200 mL) and water (200 mL). The aqueous layer was extracted again with ether (200 mL). The combined organic extracts were washed with water (1×100 mL) and brine (1×100 mL), dried over sodium sulfate, filtered and concentrated in vacuo to yield 3.88 g (35% for three steps) of 2-(4-hydroxymethyl-5-ethyl-2-methoxy-phenyl)-6-(N-2,2-dimethylpropamido)-pyridine (20) as a white semisolid. The 2-(4-hydroxymethyl-5-ethyl-2-methoxy-phenyl)-6-(N-2,2-dimethylpropamido)-pyridine (20) was washed with ether and dried.

$^1$H NMR (CDCl$_3$): 1.19 (t-3H), 1.35 (s-9H), 2.60 (q-2H; J=7.47 Hz), 3.12 (t-1H; J=6.22 Hz), 3.67 (s-3H), 4.73 (m-2H), 6.90 (s-1H), 7.36 (s-1H), 7.41 (dd-1H; J=0.83, 7.47 Hz), 7.70 (t-1H; J=8.09 Hz), 8.22 (dd-1H; J=0.83, 8.30 Hz), 8.52 (s-1H).

Preparation 17

2-(4-formyl-5-ethyl-2-methoxy-phenyl)-6-(N-2,2-dimethylpropamido)-pyridine (21)

Under a nitrogen atmosphere, 1.98 g (2.28 mmol) of MnO$_2$ was added to a toluene (50 mL) solution containing 1.56 g (4.56 mmol) of 2-(4-hydroxymethyl-5-ethyl-2-methoxy-phenyl)-6-(N-2,2-dimethylpropamido)-pyridine (20). The solution was allowed to stir for 18 hours at 90° C. The reaction mixture was then cooled and concentrated in vacuo. The resultant residue was partitioned between ethyl acetate (200 mL) and water (200 mL). The aqueous layer was extracted again with ethyl acetate (2×200 mL). The combined organic extracts were dried over sodium sulfate, filtered and concentrated in vacuo to yield crude product. The crude product was chromatographed on a silica gel column with 20% ether in hexane followed by 50% ether in hexane to afford 1.29 g (83%) of 2-(4-formyl-5-ethyl-2-methoxy-phenyl)-6-(N-2,2-dimethylpropamido)-pyridine (21).

$^1$H NMR (CDCl$_3$): 1.19 (t-3H), 1.34 (s-9H), 2.60 (q-2H; J=7.48 Hz), 3.89 (s-3H) 7.46 (s-1H), 7.56 (dd-1H; J=0.83, 7.69 Hz), 7.63 (s-1H), 7.73 (t-1H; J=7.69 Hz), 8.05 (bs-1H), 8.22 (dd-1H; J=0.83, 8.30 Hz), 10.35 (s-1H).

Preparation 18

2-(4-N,N-dimethylaminomethyl-5-ethyl-2-methoxy-phenyl)-6-(N-2,2-dimethylpropamido)-pyridine (22)

Under a nitrogen atmosphere, 330 mg (0.97 mmol) of 2-(4-formyl-5-ethyl-2-methoxy-phenyl)-6-(N-2,2-dimethylpropamido)-pyridine (21), 3 mL (6.00 mmol) of 2M N,N-dimethylamine in THF, 390 mg (1.84 mmol) of sodium triacetoxyborohydride and 120 uL (1.94 mmol) of acetic acid were combined in dichloromethane (5 mL). The solution was allowed to stir for 5 hours at 23° C. The reaction mixture was then washed with 1 M NaOH. The aqueous layer was extracted again with dichloromethane (2×50 mL). The combined organic extracts were dried over sodium sulfate, filtered and concentrated in vacuo to yield crude product. The crude product was chromatographed on a silica gel column with 10% methanol in dichloromethane to afford 367 mg (100%) of 2-(4-N,N-dimethylaminomethyl-5-ethyl-2-methoxy-phenyl)-6-(N-2,2-dimethylpropamido)-pyridine (22).

$^1$H NMR (CDCl$_3$): 1.20 (t-3H), 1.31 (s-9H), 2.30 (s-6H), 2.69 (q-2H; J=7.48 Hz), 3.48 (s-2H), 3.83 (s-3H), 7.08 (s-1H), 7.48–7.52 (m-2H), 7.69 (t-1H), 8.10 (bs-1H), 8.15 (d-1H; J=8.30 Hz).

EXAMPLE 3

6-[4-(N,N-dimethylaminomethyl)-5-ethyl-2-methoxy-phenyl]-pyridin-2-ylamine (23)

Under a nitrogen atmosphere, 367 mg (0.97 mmol) of 2-(4-N,N-dimethylaminomethyl-5-ethyl-2-methoxy-phenyl)-6-(N-2,2-dimethylpropamido)-pyridine (22) and 10 mL of 6N HCl were combined in 10 mL of dioxane. The reaction was allowed to reflux with stirring for 16 hours, allowed to cool to ambient temperature, and diluted with 1M NaOH until the solution was basic. The resultant solution was extracted with dichloromethane (3×50 mL). The combined organic extracts were dried over sodium sulfate, filtered and concentrated in vacuo to yield crude product. The crude product was chromatographed on a silica gel column with 80% ethyl acetate in hexane followed by 10% methanol in dichloromethane to afford 137 mg (49%) of 6-[4-(N,N-dimethylaminomethyl)-5-ethyl-2-methoxy-phenyl]-pyridin-2-ylamine (23).

$^1$H NMR (CDCl$_3$): 1.19 (t-3H), 2.25 (s-6H), 2.66 (q-2H; J=7.68 Hz), 3.41 (s-2H), 3.82 (s-3H), 4.41 (bs-2H), 6.42 (d-1H; J=8.10 Hz), 6.99 (s-1H), 7.14 (d-1H; J=7.48 Hz), 7.43–7.49 (m-2H).

Preparation 19

2-(4-N-methylaminomethyl-5-ethyl-2-methoxy-phenyl)-6-(N-2,2-dimethylpropamido)-pyridine (24)

Under a nitrogen atmosphere, 830 mg (2.44 mmol) of 2-(4-formyl-5-ethyl-2-methoxy-phenyl)-6-(N-2,2-dimethylpropamido)-pyridine (21), 12.2 mL (24.4 mmol) of 2M N-methylamine in THF and 979 mg (4.62 mmol) of sodium triacetoxyborohydride were combined in dichloromethane (25 mL). The resultant solution was stirred for 12 hours. 1.82 mL (32.9 mmol) of acetic acid was added, followed by another 979 mg (4.62 mmol) of sodium triacetoxyborohydride. The solution was allowed to stir for an additional 12 hours at 23° C. The reaction mixture was then washed with 1N NaOH. The aqueous layer was extracted again with dichloromethane (3×50 mL). The combined organic extracts were dried over sodium sulfate, filtered and concentrated in vacuo to yield crude product. The crude product was chromatographed on a silica gel column with 5-10% methanol in dichloromethane to afford 551 mg (64%) of 2-(4-N-methylaminomethyl-5-ethyl-2-methoxy-phenyl)-6-(N-2,2-dimethylpropamido)-pyridine (24).

$^1$H NMR (CDCl$_3$): 1.23 (t-3H; J=7.48 Hz), 1.32 (s-9H), 1.56 (bs-1H), 2.52 (s-3H), 2.69 (q-2H; J=7.48 Hz), 3.79 (s-2H), 3.83 (s-3H), 7.03 (s-1H), 7.49–7.51 (m-2H), 7.69 (t-1H: J=7.89 Hz), 8.05 (bs-1H), 8.15 (d-1H; J=7.89 Hz).

EXAMPLE 4

6-[4-(N-methylaminomethyl)-5-ethyl-2-methoxy-phenyl]-pyridin-2-ylamine (25)

Under a nitrogen atmosphere, 550 mg (1.55 mmol) of 2-(4-N-methylaminomethyl-5-ethyl-2-methoxy-phenyl)-6-(N-2,2-dimethylpropamido)-pyridine (24) and 30 mL of 6N HCl were combined in 30 mL of dioxane. The reaction was allowed to reflux with stirring for 48 hours, allowed to cool to ambient temperature, and diluted with 1N NaOH until the solution was basic. The resultant solution was extracted with dichloromethane (3×50 mL). The combined organic extracts were dried over sodium sulfate, filtered and concentrated in vacuo to yield crude product. The crude product was chromatographed on a silica gel column with 80% ethyl acetate in hexane, followed by 10%-15% methanol in dichloromethane, to afford 290 mg (69%) of 6-[4-(N-methylaminomethyl)-5-ethyl-2-methoxy-phenyl]-pyridin-2-ylamine (25).

$^1$H NMR (CDCl$_3$): 1.19 (t-3H; J=7.47 Hz), 1.80 (bs-1H), 2.50 (s-3H), 2.65 (q-2H), J=7.47 Hz), 3.77 (s-2H), 3.82 (s-3H), 4.44 (bs-2H), 6.42 (d-1H; J=8.30 Hz), 6.99 (s-1H), 7.13 (d-1H; J=7.89 Hz), 7.44 (t-1H; J=7.89 Hz), 7.51 (s-1H).

What is claimed is:

1. A compound selected from the group consisting of:

6-[4-(N-methyl-3-azetidinoxy)-5-ethyl-2-methoxy-phenyl]-pyridin-2-ylamine;

6-[4-(N,N-dimethylaminomethyl)-5-ethyl-2-methoxy-phenyl]-pyridin-2-ylamine;

6-[4-(N-methylaminomethyl)-5-ethyl-2-methoxy-phenyl]-pyridin-2-ylamine; and

6-[4-(3-azetidinoxy)-5-ethyl-2-methoxy-phenyl]-pyridin-2-ylamine; and any pharmaceutically acceptable salt of any of said compounds.

2. A compound according to claim 1, wherein said compound is 6-[4-(N-methyl-3-azetidinoxy)-5-ethyl-2-methoxy-phenyl]-pyridin-2-ylamine, or a pharmaceutically acceptable salt thereof.

3. A compound according to claim 1, wherein said compound is 6-[4-(N,N-dimethylaminomethyl)-5-ethyl-2-methoxy-phenyl]-pyridin-2-ylamine, or a pharmaceutically acceptable salt thereof.

4. A compound according to claim 1, wherein said compound is 6-[4-(N-methylaminomethyl)-5-ethyl-2-methoxy-phenyl]-pyridin-2-ylamine, or a pharmaceutically acceptable salt thereof.

5. A compound according to claim 1, wherein said compound is 6-[4-(3-azetidinoxy)-5-ethyl-2-methoxy-phenyl]-pyridin-2-ylamine, or a pharmaceutically acceptable salt thereof.

* * * * *